United States Patent
Chen et al.

(10) Patent No.: US 11,690,544 B2
(45) Date of Patent: **\*Jul. 4, 2023**

(54) METHOD OF PRODUCING THIN ENZYME-BASED SENSING LAYERS ON PLANAR SENSORS

(71) Applicant: CALIFORNIA INSTITUTE OF TECHNOLOGY, Pasadena, CA (US)

(72) Inventors: Samson Chen, Pasadena, CA (US); Axel Scherer, Barnard, VT (US); Dvin Adalian, Pasadena, CA (US); Peter Petillo, Pasadena, CA (US); Muhammad Musab Jilani, Pasadena, CA (US); Xiomara L. Madero, Pasadena, CA (US); Deepan Kishore Kumar, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 17/314,930

(22) Filed: May 7, 2021

(65) Prior Publication Data

US 2021/0321918 A1    Oct. 21, 2021

Related U.S. Application Data

(63) Continuation of application No. 16/144,079, filed on Sep. 27, 2018, now Pat. No. 11,026,610.

(60) Provisional application No. 62/564,914, filed on Sep. 28, 2017.

(51) Int. Cl.
| | |
|---|---|
| A61B 5/145 | (2006.01) |
| C12N 11/02 | (2006.01) |
| A61B 5/1486 | (2006.01) |
| C12N 9/02 | (2006.01) |
| A61B 5/1459 | (2006.01) |
| G01N 27/327 | (2006.01) |
| C12N 11/14 | (2006.01) |

(52) U.S. Cl.
CPC ........ *A61B 5/14865* (2013.01); *A61B 5/1459* (2013.01); *A61B 5/14532* (2013.01); *C12N 9/0004* (2013.01); *C12N 11/02* (2013.01); *C12N 11/14* (2013.01); *G01N 27/3272* (2013.01); *C12Y 101/01001* (2013.01); *C12Y 101/0301* (2013.01); *C12Y 101/0302* (2013.01); *C12Y 101/03003* (2013.01); *C12Y 101/0303* (2013.01); *C12Y 101/03004* (2013.01); *C12Y 101/03005* (2013.01); *C12Y 101/03007* (2013.01); *C12Y 101/03008* (2013.01); *C12Y 101/03011* (2013.01); *C12Y 101/03012* (2013.01); *C12Y 101/03015* (2013.01); *C12Y 101/03016* (2013.01); *C12Y 101/03018* (2013.01); *C12Y 101/03019* (2013.01); *C12Y 101/03023* (2013.01); *C12Y 101/03027* (2013.01); *C12Y 101/03029* (2013.01); *C12Y 101/03037* (2013.01); *C12Y 101/03038* (2013.01); *C12Y 101/03041* (2013.01)

(58) Field of Classification Search
CPC ............ A61B 5/14865; A61B 5/14532; A61B 5/1459; C12N 9/0004; C12N 11/02; C12N 11/14; G01N 27/3272; C12Y 101/01001; C12Y 101/03003; C12Y 101/03005; C12Y 101/03007; C12Y 101/03008; C12Y 101/0301; C12Y 101/03011; C12Y 101/03012; C12Y 101/03015; C12Y 101/03016; C12Y 101/03018; C12Y 101/03019; C12Y 101/0302; C12Y 101/03023; C12Y 101/03027; C12Y 101/03029; C12Y 101/0303; C12Y 101/03037; C12Y 101/03038; C12Y 101/0304; C12Y 101/03041; C12Q 1/001; C12Q 1/005
See application file for complete search history.

(56) References Cited

U.S. PATENT DOCUMENTS

| | | | |
|---|---|---|---|
| 6,485,703 B1 * | 11/2002 | Cote et al. | 424/9.1 |
| 8,497,106 B2 | 7/2013 | Suarez | |
| 11,026,610 B2 | 6/2021 | Chen et al. | |
| 2009/0062767 A1 | 3/2009 | Van Antwerp et al. | |
| 2010/0030045 A1 * | 2/2010 | Gottlieb et al. | 600/347 |
| 2019/0090796 A1 | 3/2019 | Chen et al. | |

FOREIGN PATENT DOCUMENTS

| | | |
|---|---|---|
| EP | 2393424 B1 | 1/2015 |
| WO | 2010/091334 A2 | 8/2010 |

OTHER PUBLICATIONS

Extended European Search Report issued for European Application No. EP 18860065.4 filed on Sep. 27, 2018 on behalf of California Institute of Technology, dated Jun. 24, 2021. 9 Pages.
Pu, Z., et al., "Cylindrical electrochemical sensor fabricated by rotated inkjet printing on flexible substrate for glucose monitoring", *2017 19th International Conference On Solid-state Sensors*, Actuators And Microsystems (Transducers), IEEE, Jun. 18, 2017, pp. 1241-1244. XP033130940, DOI: 10.1109/TRANSDUCERS.2017. 79 94280.

\* cited by examiner

*Primary Examiner* — Satyendra K Singh
(74) *Attorney, Agent, or Firm* — Steinfl + Bruno, LLP

(57) ABSTRACT

A sensor implanted in tissues and including a sensing layer is fabricated by mixing the signal transduction enzyme with non-reactive components including buffer salts and fillers, and spin coating the enzyme onto a substrate. The signal transduction enzyme is crosslinked by introducing the coated substrate in a vacuum chamber. In the chamber, a crosslinker evaporates and is deposited onto the enzyme, therefore crosslinking the enzyme.

14 Claims, 6 Drawing Sheets

METHOD OF PRODUCING THIN ENZYME-BASED SENSING LAYERS ON PLANAR SENSORS

CROSS REFERENCE TO RELATED APPLICATIONS

The present application is a continuation of U.S. patent application Ser. No. 16/144,079, filed on Sep. 27, 2018, which claims priority to U.S. Provisional Patent Application No. 62/564,914, filed on Sep. 28, 2017, the contents of all of which are incorporated herein by reference in their entireties.

TECHNICAL FIELD

The present disclosure relates to biosensing. More particularly, it relates to a method of producing thin enzyme-based sensing layers on planar sensors.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

Figure 1:
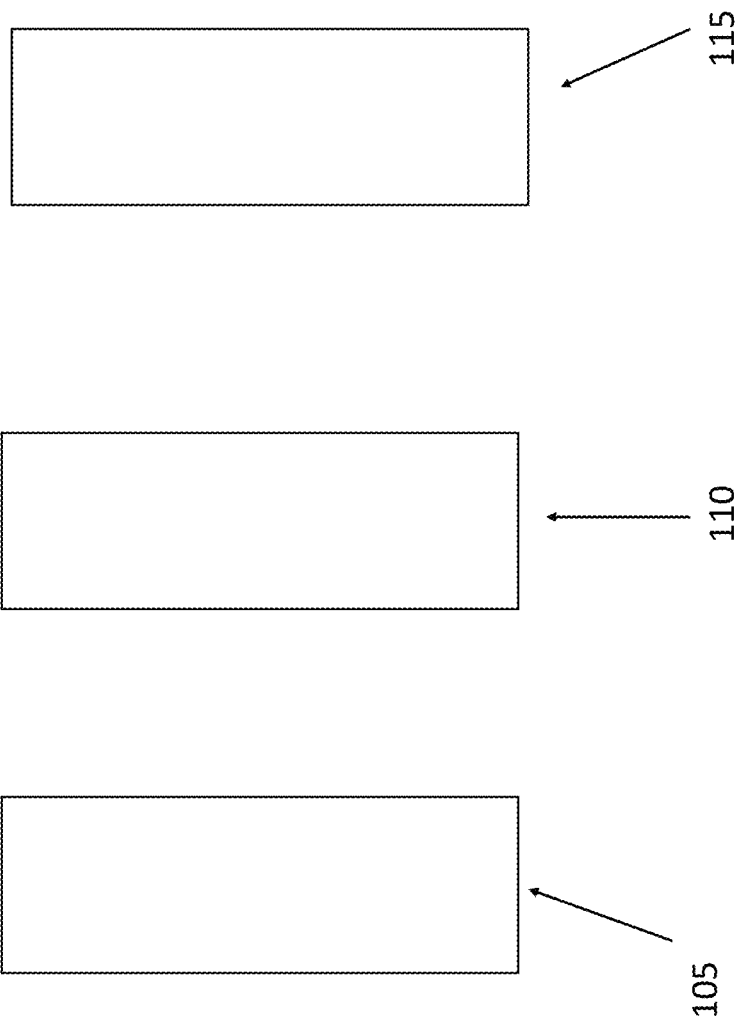
FIG. 1 illustrates a sensor with three electrodes.

The present disclosure describes small, minimally-invasive implantable sensors. These sensors can help improve medical outcomes in many situations. For example, many diabetics can benefit from continuous glucose sensing, to manage their insulin and food intake. Unfortunately, some of the requirements of such sensors—e.g., being small and accurate—are contradictory when using presently available technologies.

Most implantable sensors capable of measuring small molecules, such as glucose, consist of at least an enzyme-based signal transduction layer, and an electrochemical sensor. Typically, the enzyme selectively generates hydrogen peroxide when acting upon a small molecule of interest, such as glucose. This active compound produces an electrical current, proportional to the concentration of the small molecule of interest, using the electrochemical sensor.

The characteristics of the enzyme-based sensing layer directly affect the performance of the sensor. As the dimensions of the sensor decrease in order to improve patient comfort, traditional coating techniques become less and less reproducible, resulting in lower manufacturing yields and poorer accuracy. Additionally, many performance characteristics of a sensor, including sensitivity and linearity, improve as the thickness of this layer decreases—but many traditional coating methods cannot deposit layers with small thicknesses in a reproducible and consistent manner.

The enzyme-based sensing layers typically have two or three primary components: a signal transduction enzyme, capable of converting a small molecule to an electroactive compound with good specificity, for example an enzyme from the oxidase family like glucose oxidase or lactate oxidase; a crosslinker, such as glutaraldehyde, which keeps the enzymes bound to each other and to the surface, so that the enzyme does not dissolve away; and optionally, a filler enzyme, such as albumin. Filler enzymes can be used to lower the cost of the device, as well as to protect the active group and conformation of the electroactive compound. According to methods known to the person of ordinary skill in the art, to deposit an enzyme layer all three compounds are mixed together prior to use, and then painted, or otherwise deposited, onto a cylindrical sensor. In some fabrication processes, the three compounds are dropped with a pipette onto a planar sensor.

The mixture of three compounds immediately begins reacting, and increasing in viscosity after mixing. Therefore, there is a very short time window in which dispensing the mixture is possible. Sensors fabricated using these methods known to the person of ordinary skill in the art frequently exhibit high variability and large coating thicknesses, due to the high and constantly changing viscosity of the mixture.

In the fabrication methods of the present disclosure, the crosslinker is not mixed with the rest of the components in the initial steps, in order to improve the repeatability of the process. In a first step, only the signal transduction enzyme, optional filler components, and any other non-reactive components, such as buffer salts to maintain the pH of the solution, are mixed together in a suitable solvent, for example water. The mixture is then coated onto a planar surface of a substrate by spin coating, a process typically used for reproducibly coating very thin (less than 1 micrometer) polymer films in the semiconductor fabrication industry. A variety of parameters, including rotational velocity, dispensing volume and rate, spin time, ramp-up rate, solvent concentration and type, and humidity, may be used to adjust the parameters, including thickness, of the final film.

For example, when spun at 2000-4000 rpm for 30 seconds, films with thicknesses between 100 and 300 nm are possible. The deposited film can then be partly dried in air or in a controlled environment, e.g. having a controlled temperature and humidity, until it is sufficiently solid for further handling. It can be noted that the deposition step of the mixture may involve the use of a mask, to ensure that the enzyme mixture is only deposited on desired areas of the planar substrate. For example, photolithography or other techniques known to the person of ordinary skill in the art can be used to prepare a mask on the substrate, deposit the enzyme mixture, and subsequently remove the mask. In some embodiments, the mask may be left in place if required for the deposition of further compounds as described below.

The second step of the fabrication process is to crosslink the film deposited in the previous step using a vapor deposition process. The crosslinker used, for example, can be glutaraldehyde, which is stable in the vapor phase. Typically, this step is performed in a vacuum chamber. For example, a solution of glutaraldehyde, and the planar substrate coated with the enzyme film are introduced into a vacuum chamber, and the pressure inside the chamber is reduced. The enzyme film is, at this stage, not yet crosslinked. Upon heating, gaseous glutaraldehyde is deposited on the previously-deposited enzyme mixture in a controlled manner. The glutaraldehyde, or another crosslinker, will then crosslink the partially dried enzyme on the surface into a robust, solid film.

In some embodiments, variations of this method may be employed. For example, fabrication steps may comprise: introducing glutaraldehyde into the vacuum chamber in gaseous form, changing the temperature of the wafer itself or of the gases, introducing or limiting the composition of gases (including water vapor) into the partial vacuum of the system, controlling chamber pressure, controlling exposure time, and controlling the gas flow inside the chamber. In the case of glutaraldehyde, an additional benefit is gained due to the use of glutaraldehyde vapor. Glutaraldehyde has complex behaviors in solution form, and exists in a variety of polymeric forms depending on the time passed since its manufacture, and storage conditions. The vapor is relatively pure, and avoiding the use of a glutaraldehyde solution can further improve reproducibility.

Subsequently, after removal of the planar substrate from the vacuum chamber, the substrate can be left in a controlled atmosphere for a period of time, preferably from about 10 minutes to about 2 hours, and more preferably about 30 minutes, in ambient air or in a high humidity chamber. This allows the cross-linker to fully react with the previously-deposited enzyme mixture. The substrate can then be stored in a liquid solution, if necessary, typically phosphate buffered saline, or in a high humidity chamber, to prevent the film from drying out and losing sensitivity.

In some embodiments using certain planar substrates, the enzyme film may exhibit poor adhesion to the exposed surfaces of the substrate. In these cases, an additional layer of an adhesion promoter may be coated onto the substrate prior to spin-coating the enzyme mixture. The adhesion promoter may be compatible with the substrate's surface, the enzyme, and the crosslinker. Sometimes, however, the adhesion layer may only be necessary on certain parts of the planar surface of the substrate, and may in fact be detrimental to sensor performance. In these cases, photolithography or another selective masking technique may be used to ensure the adhesion promoter is only coated onto particular areas of the substrate.

For example, a thin enzyme film, produced with the previously described method, can be coated directly onto a complementary metal-oxide semiconductor (CMOS) integrated circuit die containing a platinum-based electrochemical sensor. Outside of the platinum electrodes, the surface of the die is typically silicon nitride, which has poor adhesion to the enzyme film. An inorganic-organic amine coupler, such as (3-aminopropyl)trimethoxysilane (APTMS) may be used to prevent the enzyme film from peeling off the substrate and causing sensor failure. This coupler can be coated onto the wafer using spin-coating or vapor deposition techniques. However, this adhesion promoter is unnecessary on the platinum electrodes, where it impedes sensor performance. Thus, a photolithographically defined mask may be used to pattern the adhesion promoter and prevent it from being applied directly to the platinum electrodes.

The fabrication process described in the present disclosure is capable of producing extremely thin, preferably less than about 10 micrometer, more preferably less than about 5 micrometers, and most preferably less than about 1 micrometer layers of enzyme-based sensing films, and benefits from the repeatability and consistency of its constituent steps. In another embodiment, the fabrications process produces films of less than about 0.5 micrometers.

Figure 3:
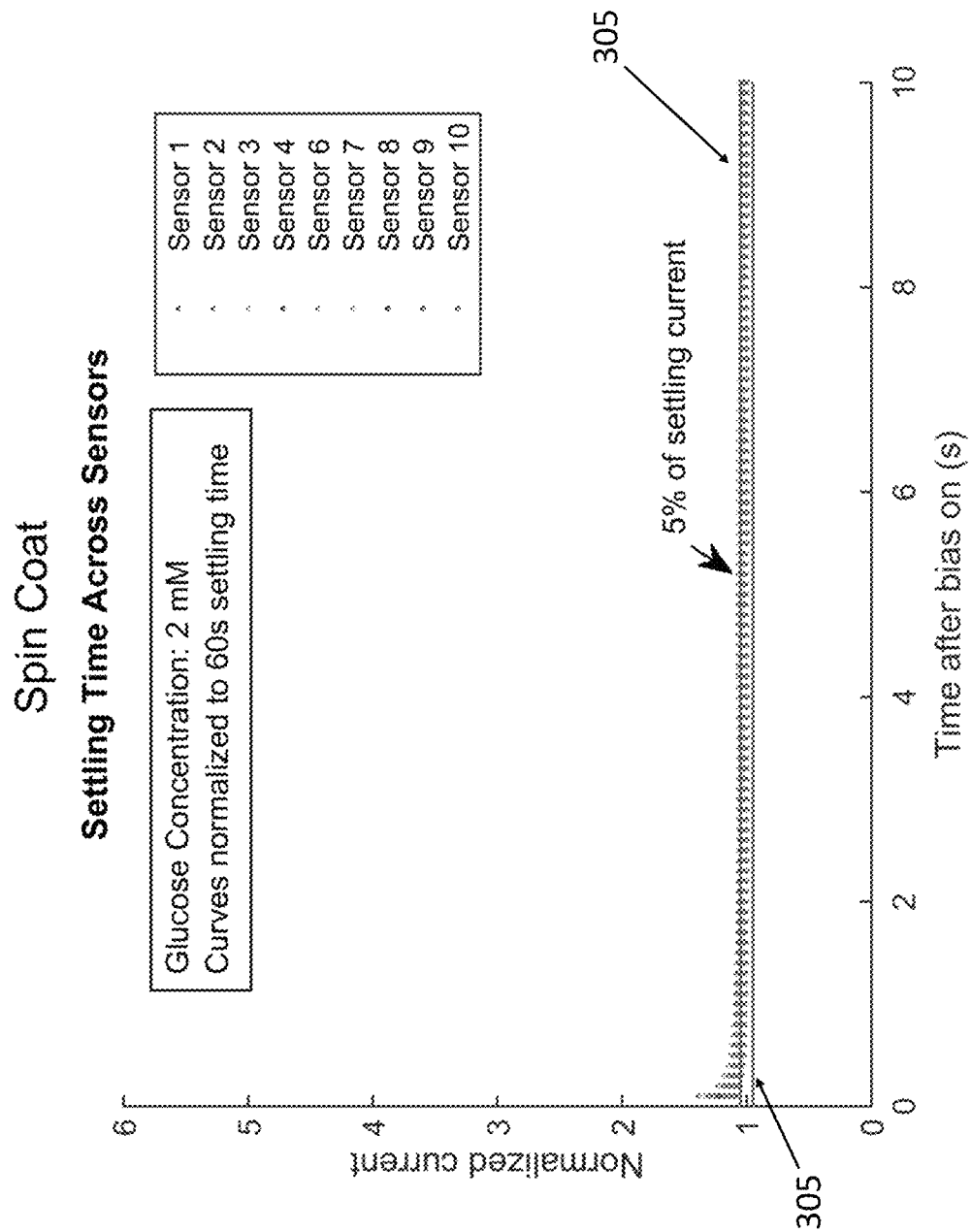
FIG. 3 and FIG. 4 illustrate exemplary time-current curves for sensors with spin-coated enzyme layers as described in the present disclosure.
Figure 4:
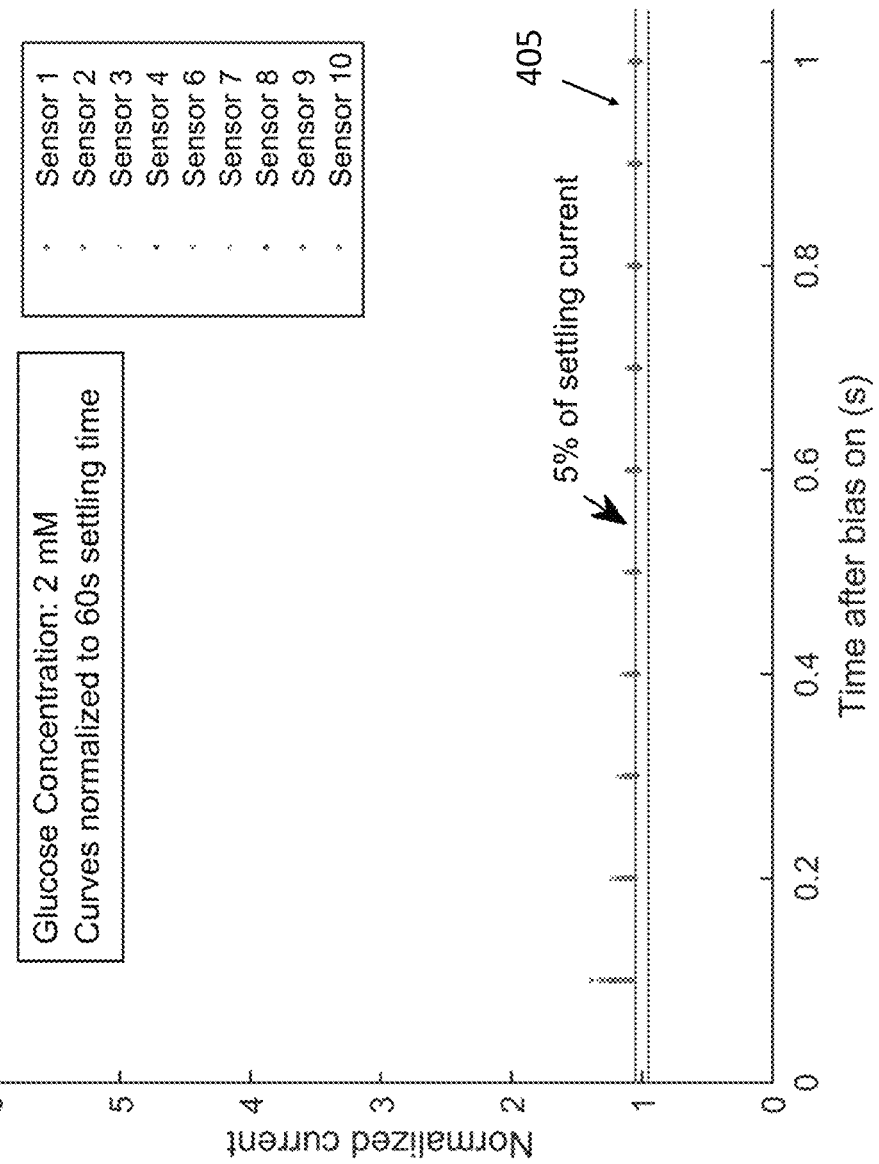
Figure 5:
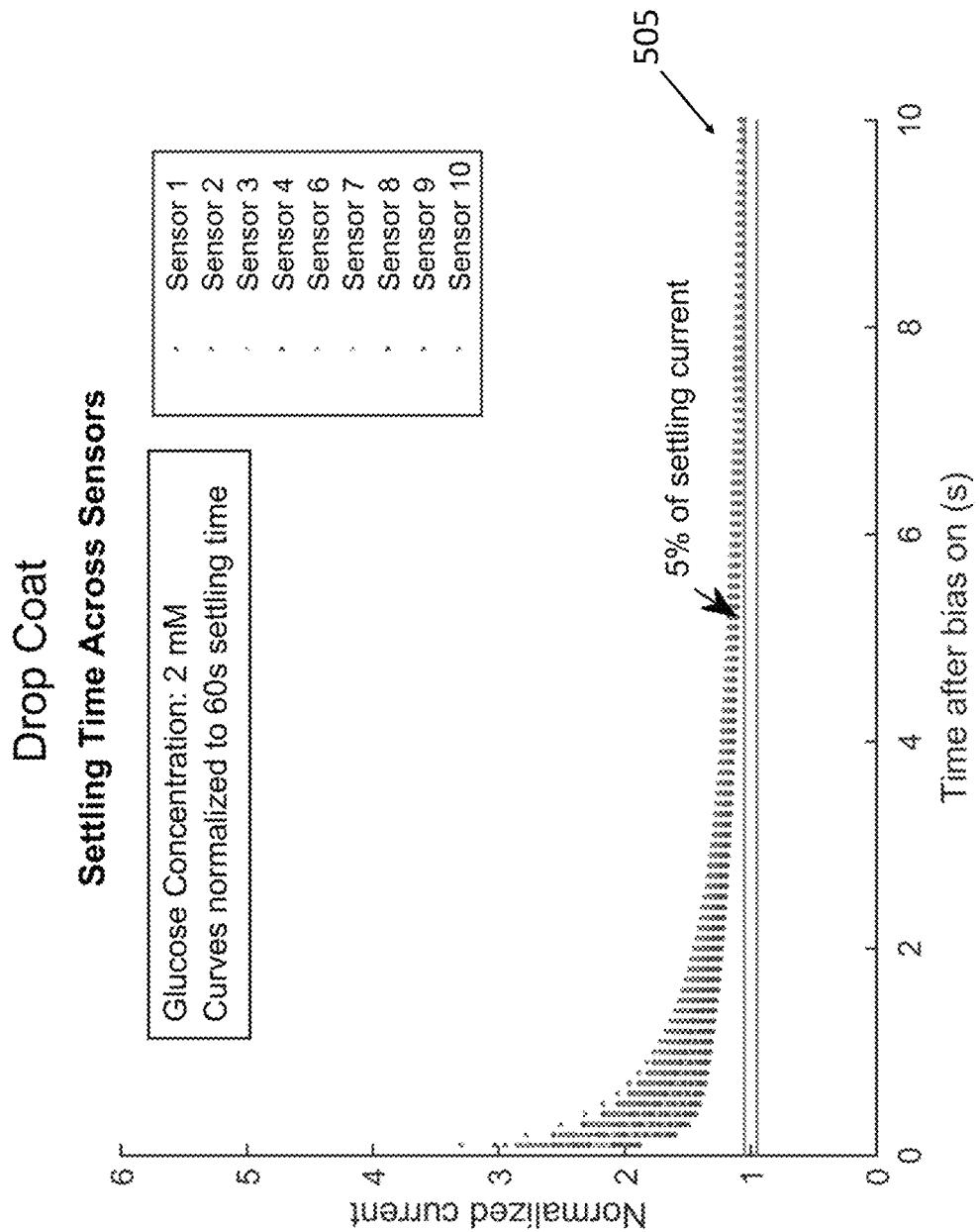
FIG. 5 and FIG. 6 illustrate exemplary time-current curves for sensors with known drop-coated enzyme layers.
Figure 6:
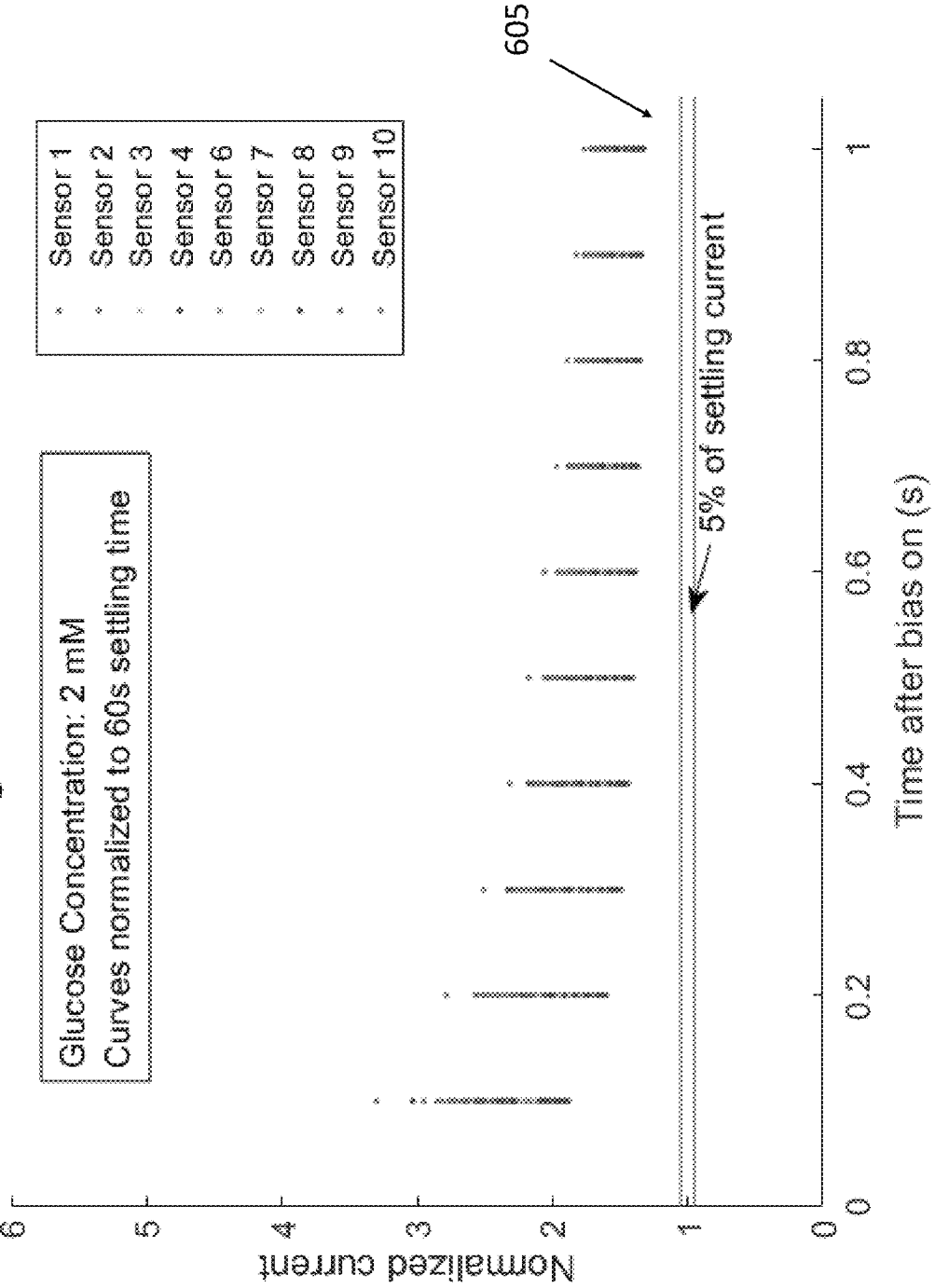

The thinness of the enzyme layers thus fabricated enables quicker diffusion through the layer, which is reflected in the measurements as a faster-stabilizing current. Therefore, the sensors fabricated according to the method of the present disclosure typically require a shorter time to reach a stable current, during measurements. Most sensors with the thin, spin-coated enzyme layers described herein show a less than about 5% deviation between: 1. the current measured 1 second after the sensor is turned on, and 2. the current measured 60 seconds after the sensor is turned on. FIG. 3 and FIG. 4 illustrate two exemplary measurements of spin coated sensors, fabricated according to the method of the present disclosure. It can be noted in FIGS. 3-4 that the current quickly settles within about 5% of the stable value, as indicated by horizontal lines (305). Most sensors with traditional thick drop-coated enzyme layers fail to fall inside this about 5% tolerance window even after 10 seconds after the sensor is turned on, as can be seen from both FIG. 5 and FIG. 6, which illustrate measurements with drop-coated sensors.

The quicker settling time allows the spin coated sensors to operate in a more efficient manner. It is now possible, for example, to turn on the sensor for shorter periods of time for each measurement, compared to the drop coated sensors. Due to the shorter activation time now required, the amount of energy necessary for each measurement is reduced. Therefore, the average power that needs to be delivered to the sensor is reduced, while keeping the same rate of measurements. FIGS. 3-6 plot measurements for different sensors. While these sensors show differences in settling time, the difference between individual sensors does not change the fact that the spin coated sensors have an overall much faster settling time, when compared to the drop coated sensors. The lines which show 5% deviations, in the upper and lower directions, of the stable current are shown in FIGS. 3-6 as (305), (405), (505) and (605).

Additionally, because all of the steps can be performed on very large substrates, the fabrication process described in the present disclosure has a very low per-sensor cost, as the enzyme film does not have to be coated individually for each sensor. For example, it is possible to simultaneously coat 50,000 electrochemical sensors, each having an area 1.2×1.2 mm, on an industry-standard 200 mm silicon wafer, using the process described above. The simultaneous fabrication of many sensors results in enormous time and cost savings over coating each sensor individually.

Therefore, in some embodiments, the fabrication process of the present disclosure comprises a method of fabricating an enzyme-based sensing layer on top of a planar substrate for electrochemical sensing according to the following steps. In a first step, an optional adhesion layer is patterned and coated on top of the planar substrate, the adhesion layer being compatible with both the substrate and compounds in the enzyme-based sensing layer. In a second step, the non-reactive components of the enzyme-based sensing layer are spin-coated onto the planar substrate. In a third step, the spin coated layer is optionally at least partially dried in a controlled atmosphere to allow the film to sufficiently solidify for handling. In a fourth step, the reactive component(s) of the enzyme-based sensing layer are vapor-deposited onto the non-reacted components of the enzyme-based sensing layer on the planar substrate. In a fifth step, the coated planar substrate is optionally left in a controlled environment to complete crosslinking. In a sixth step, the coated planar substrate is optionally stored in a controlled environment known to the person of ordinary skill in the art, to prevent drying of the enzyme layer.

In some embodiments, the planar substrate contains a sensor with a 2 electrode setup, or a 3 electrode setup. A two-electrode setup includes a working electrode, on which the reaction of interest occurs, and a counter electrode, which completes the circuit. A three-electrode setup additionally includes a reference electrode which does not source or sink current, but which is used as a fixed-potential electrode with respect to which the potential of the working electrode is maintained. In some embodiments, additional electrodes are used, such as to complete the circuit for an electrode surface activation or passivation reaction for one electrode, without affecting the surface condition of the other electrodes. In some embodiments, the electrodes are composed of platinum, silver chloride, silver oxide, silver oxide, or a combination of these materials. In some embodiments, the non-reactive components are an oxidase enzyme and albumin, and the reactive component is glutaraldehyde. In some embodiments, the planar substrate is a silicon-based device, such as an electrochemical cell fabricated on a bare silicon wafer or a silicon wafer containing additional circuitry. In some embodiments, the adhesion promoter of the first step is an aminosilane, such as 3-aminopropyltriethoxysilane (APTES), 3-aminopropyltrimethoxysilane (APTMS), or similar, and the coating method of the adhesion layer is spin-coating or vapor deposition. In some embodiments, the adhesion promoter layer is patterned using photolithography to prevent deposition of the promoter onto the electrodes while allowing the deposition of the promoter on other areas of the underlying substrate where the enzyme will be subsequently deposited.

As illustrated in FIG. 1, a sensor comprising the sensing layers fabricated by the methods of the present disclosure may comprise a platinum working electrode (105), at which the hydrogen peroxide (e.g. for the case of glucose sensing) is consumed, a platinum counter electrode (115) that completes the circuit, and a platinum reference electrode (110), with respect to which the potential of the working electrode is maintained. In some embodiments, the enzyme is an oxidase enzyme, such as glucose oxidase, lactate oxidase, uricase oxidase, urease oxidase or other enzymes from the oxidase family.

Figure 2:
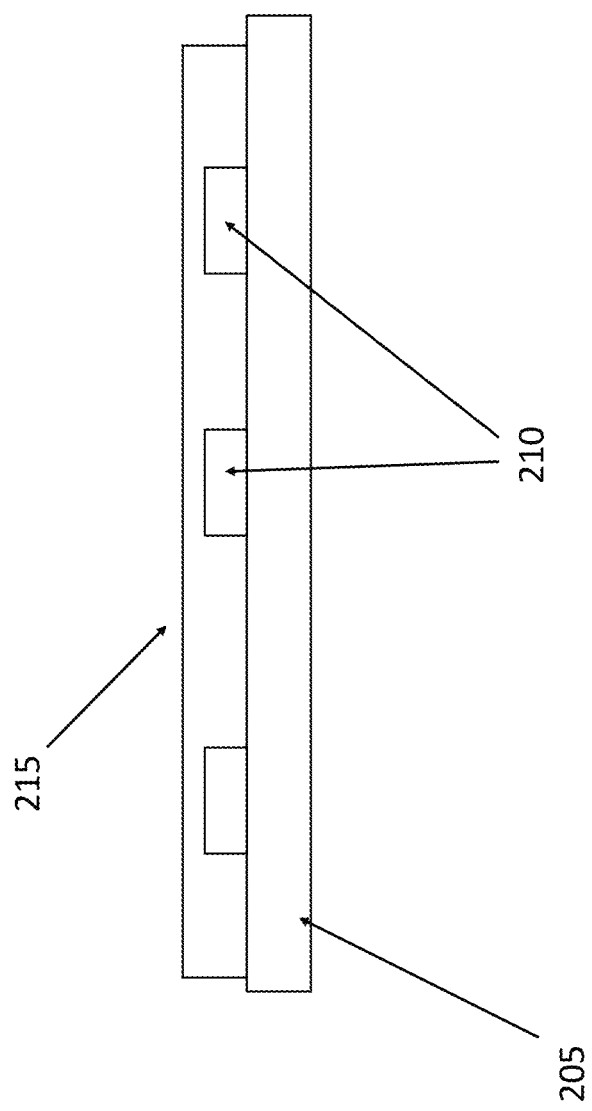
FIG. 2 illustrates a sensor with a signal transduction enzyme.

FIG. 2 illustrates a 3-electrode setup comprising a substrate (205), electrodes (210), and a signal transduction enzyme (215). In some embodiments, the signal transduction enzyme is configured so that a current measured by the plurality of electrodes settles within about 5% of its stable value within 1 second, or less than a second, or less than 2 seconds. It can be seen from FIGS. 3-6 that the drop coated sensors do not settle within even 2 seconds to the stable current value.

In some embodiments, a crosslinker may be homobifunctional. In general, a homobifunctional crosslinking agent has two reactive groups which are identical and located at the ends of an organic spacer arm. The length of the organic spacer may be modified to optimize the distance between the two molecules to be conjugated. For example, homobifunctional crosslinking agents comprise: Lomant's reagent, Dithiobis(succinimidylpropionate) (DSP), Dithio bis(sulfosuccinimidyl propionate) (DTSSP), Disuccinimidyl suberate (DSS), Bis(sulfosuccinimidyl) suberate (B $S^3$), Disuccinimidyl tartrate (DST), Disulfosuccinimidyl tartrate (sulfo-DST), bis[2-(succinimidyloxycarbonyloxy)ethyl]sulfone (BSOCOES), bis[2-(sulfosuccinimidooxycarbonyloxy)ethyl]sulfone] (Sulfo-BSOCOES), Ethylene glycol bis(succinimidylsuccinate) (EGS), Ethylene glycol bis(sulfosuccinimidylsuccinate) (Sulfo-EGS), Disuccinimidyl glutarate (DSG), N,N'-Disuccinimidyl carbonate (DSC), Dimethyl adipimidate (DMA), Dimethyl pimelimidate (DMP), Dimethyl suberimidate (DMS), Dimethyl 3,3'-dithiobispropionimidate (DTBP), 1,4-di-[3'-(2'-pyridyldithio)propionamido]butane (DPDPB), Bis-maleimidohexane (BMH), 1,5-Difluoro-2,4-dinitrobenzene (DFDNB), 4,4'-Difluoro-3,3'-dinitrophenylsulfone (DFDNPS), Bis-[☐-(4-azidosalicylamido)ethyl]disulfide (BASED), Formaldehyde, Glutaraldehyde, 1,4-Butanediol Diglycidyl Ether, Adipic Acid Dihydrazide (ADH), Carbohydrazide, o-Tolidine, Diazotized, Bis-diazotized Benzidine, 1,3-dibromoacetone and various iodoacetyl derivatives of short diamine alkyl spacers, N,N'-ethylene-bis(iodoacetamide), N,N'-Hexamethylene-bis(iodoacetamide), N,N'-Undecamethylene-bis(iodoacetamide), bis-NHS-$PEG_x$, 1,8-bis-maleimido-diethyleneglycol (BM[PEG]2), 1,11-bis-maleimido-triethyleneglycol (BM[PEG]$_3$), bis-MAL-$dPEG®_x$, PEGylated bis (sulfosuccinimidyl)suberate ($BS^3$(PEG)5), PEGylated bis (sulfosuccinimidyl)suberate ($BS^3$(PEG)9), 2,2-disulfanediylbis(2-methylpropanal), Isophthalaldehyde, Terephthalaldehyde, Neopentyl glycol diglycidyl ether, Poly(ethylene glycol) diglycidyl ether, 1,2,7,8-Diepoxyoctane, 4-(4-Formylphenoxy)benzaldehyde, 4-[2-(4-formylphenoxy)ethoxy]benzaldehyde, Resorcinol diglycidyl ether, and adipaldehyde.

In some embodiments, a crosslinker may be heterobifunctional. In general, a heterobifunctional crosslinking agent includes two different reactive groups at either end of an organic spacer arm. The length of the organic spacer may be modified to optimize the optimal distance between the two molecules to be conjugated. For example, heterobifunctional crosslinkers comprise: N-succinimidyl-3-(2-pyridyldithio) propionate (SPDP), succinimidyl 6-(3(2-pyridyldithio)propionamido)hexanoate (LC-SPDP), sulfosuccinimidyl 6-[3'-(2-pyridyldithio)propionamido]hexanoate (sulfo-LC-SPDP), succinimidyloxycarbonyl-α-methyl-α-(2-pyridyldithio)toluene (SMPT), sulfosuccinimidyl-6-[α-methyl-α-(2-pyridyldithio)toluamido]hexanoate (sulfo-LC-SMPT), succinimidyl-4-(N-maleimidomethyl)cyclohexane-1-carboxylate (SMCC), sulfosuccinimidyl-4-(N-maleimidomethyl)cyclohexane-1-carboxylate (Sulfo-SMCC), m-maleimidobenzoyl-N-hydroxysuccinimide ester (MBS), m-maleimidobenzoyl-N-hydroxysulfosuccinimide ester (Sulfo-MBS), N-succinimidyl(4-iodoacetyl)aminobenzoate (SIAB), sulfosuccinimidyl(4-iodoacetyl)aminobenzoate (Sulfo-SIAB), succinimidyl-4-(p-maleimidophenyl)butyrate (SMPB), sulfosuccinimidyl-4-(p-maleimidophenyl)butyrate (sulfo-SMPB), N-(γ-maleimidobutyryloxy) succinimide ester (GMBS), N-(γ-maleimidobutyryloxy)sulfosuccinimide ester (Sulfo-GMBS), succinimidyl-6-((iodoacetyl)amino)hexanoate (SIAX), succinimidyl-6-(6-(((4-iodoacetyl)amino)hexanoyl)amino)hexanoate (SIAXX), succinimidyl-4-(((iodoacetyl)amino)methyl)cyclohexane-1-carboxylate (SIAC), succinimidyl-6-((((4-(iodoacetyl) amino)methyl)cyclohexane-1-carbonyl)amino) hexanoate (SIACX), p-nitrophenyl iodoacetate (NPIA), 4-(4-N-maleimidophenyl)butyric acid hydrazide (MPBH), 4-(N-maleimidomethyl)cyclohexane-1-carboxyl-hydrazide ($M_2C_2H$), 3-(2-pyridyldithio)propionyl hydrazide (PDPH), N-hydroxysuccinimidyl-4-azidosalicylic acid (NHS-ASA), sulfosuccinimidyl-2-(p-azidosalicylamido)ethyl-1,3'-dithiopropionate (SASD), N-hydroxysuccinimidyl-4-azidobenzoate (HSAB), N-hydroxysulfo succinimidyl-4-azidobenzoate (Sulfo-HSAB), N-succinimidyl-6-(4'-azido-2'-nitrophenylamino)hexanoate (SANPAH), N-5-azido-2-nitrobenzoyloxysuccinimide (ANB-NOS), Sulfosuccinimidyl-2-(m-azido-o-nitrobenzamido)-ethyl-1,3'-dithiopropionate (SAND), N-succinimidyl-(4-azidophenyl)1,3'-dithiopropionate (SADP), sulfosuccinimidyl-4-(p-azidophenyl)butyrate (Sulfo-SAPB), Sulfosuccinimidyl-2-(7-azido-4-methylcoumarin-3-acetamide)ethyl-1,3'-dithiopropionate (SAED), sulfosuccinimidyl-7-azido-4-methylcoumarin-3-acetate (Sulfo-SAMCA), p-nitrophenyl diazopyruvate (pNPDP), p-nitrophenyl-2-diazo-3,3,3-trifluoropropionate (PNP-DTP), 1-(p-azidosalicylamido)-4-(iodoacetamido)butane (ASIB), N-[4-(p-azidosalicylamido)butyl]-3'-(2'- pyridyldithio) propionamide (APDP), benzophenone-4-iodoacetamide, Benzophenone-4-maleimide, p-azidobenzoyl hydrazide (ABH), 4-(p-azidosalicylamido)butylamine (ASBA), p-azidophenyl glyoxal (APG), NHS-PEG$_x$-maleimide (x=2, 4, 6, 8, 12, 24), NHS-PEG$_x$-azide (x=4, 8, 12), and propargyl-PEG$_1$-NHS.

In some embodiments, a crosslinker may be trifunctional. In general, a trifunctional crosslinking agent includes three complexing or reactive groups per molecule. The complexing or reactive groups can be the same or different. The trifunctional approach incorporates elements of the heterobifunctional concept, where two ends of the organic linker contain reactive groups able to couple with two different functional groups on target molecules. However, a third arm is present which contains a moiety designed to specifically link to a third chemical or biological target. For example, trifunctional crosslinking agents comprise: 4-azido-2-nitrophenylbiocytin-4-nitrophenyl ester (ABNP), sulfosuccinimidyl-2-[6-(biotinamido)-2-(p-azidobenzamido)hexanoamido]ethyl-1,39-tithiopropionate (sulfo-SBED), Tris(hydroxymethyl)phosphine (THP), and β-[tris(hydroxymethyl)phosphino]propionic acid (HPP).

In some embodiments, within the classification of oxidase proteins, the preferred targets are those used in human health monitoring applications. For example, other oxidase enzymes that may be used comprise: malate oxidase, EC 1.1.3.3, hexose oxidase, EC 1.1.3.5, aryl-alcohol oxidase, EC 1.1.3.7, L-gulonolactone oxidase, EC 1.1.3.8, pyranose oxidase, EC 1.1.3.10, L-sorbose oxidase, EC 1.1.3.11, pyridoxine 4-oxidase, EC 1.1.3.12, (S)-2-hydroxy-acid oxidase, EC 1.1.3.15, ecdysone oxidase, EC 1.1.3.16, secondary-alcohol oxidase, EC 1.1.3.18, 4-hydroxymandelate oxidase, EC 1.1.3.19, long-chain-alcohol oxidase, EC 1.1.3.20, thiamine oxidase, EC 1.1.3.23, hydroxyphytanate oxidase, EC 1.1.3.27., N-acylhexosamine oxidase, EC 1.1.3.29, polyvinyl-alcohol oxidase, EC 1.1.3.30, D-Arabinono-1,4-lactone oxidase, EC 1.1.3.37, vanillyl-alcohol oxidase, EC 1.1.3.38, D-mannitol oxidase, EC 1.1.3.40, alditol oxidase, EC 1.1.3.41, choline dehydrogenase, EC 1.1.99.1, gluconate 2-dehydrogenase EC 1.1.99.3, glucooligosaccharide oxidase, EC 1.1.99.B3, alcohol dehydrogenase, EC 1.1.99.8, cellobiose dehydrogenase, EC 1.1.99.18, aldehyde oxidase, EC 1.2.3.1, glyoxylate oxidase, EC 1.2.3.5, indole-3-acetaldehyde oxidase, aryl-aldehyde oxidase, EC 1.2.3.9, retinal oxidase, EC 1.2.3.11, abscisic-aldehyde oxidase, EC 1.2.3.14, aldehyde ferredoxin oxidoreductase, EC 1.2.7.5, indolepyruvate ferredoxin oxidoreductase, EC 1.2.7.8, aldehyde dehydrogenase, EC 1.2.99.7, dihydroorotate oxidase, EC 1.3.3.1, acyl-CoA oxidase, EC 1.3.3.6, dihydrouracil oxidase, EC 1.3.3.7, tetrahydroberberine oxidase, EC 1.3.3.8, tryptophan alpha,beta-oxidase, EC 1.3.3.10, L-galactonolactone oxidase, EC 1.3.3.12, acyl-CoA dehydrogenase, EC 1.3.99.3, Isoquinoline-1-oxidoreductase, EC 1.3.99.16, quinaldate 4-oxidoreductase, EC 1.3.99.18, D-aspartate oxidase, EC 1.4.3.1, L-amino-acid oxidase, EC 1.4.3.2, monoamine oxidase, EC 1.4.3.4, pyridoxal 5'-phosphate synthase, EC 1.4.3.5, D-glutamate oxidase, EC 1.4.3.7, ethanolamine oxidase, EC 1.4.3.8; putrescine oxidase, EC 1.4.3.10, cyclohexylamine oxidase, EC 1.4.3.12, protein-lysine 6-oxidase, EC 1.4.3.13, D-glutamate(D-aspartate) oxidase, EC 1.4.3.15, L-lysine 6-oxidase, EC 1.4.3.20, primary-amine oxidase, EC 1.4.3.21, 7-chloro-L-tryptophan oxidase, EC 1.4.3.23, N-methyl-L-amino-acid oxidase, EC 1.5.3.2, non-specific polyamine oxidase, EC 1.5.3.B2, N8-acetylspermidine oxidase (propane-1,3-diamine-forming), EC 1.5.3.B3, N6-methyl-lysine oxidase, EC 1.5.3.4, polyamine oxidase (propane-1,3-diamine-forming), EC 1.5.3.B4, N1-acetylpolyamine oxidase, EC 1.5.3.B5, spermine oxidase, EC 1.5.3.B6, pipecolate oxidase, EC 1.5.3.7, dimethylglycine oxidase, EC 1.5.3.10, polyamine oxidase, EC 1.5.3.11, Dihydrobenzophenanthridine oxidase, EC 1.5.3.12, NAD(P)H oxidase, EC 1.6.3.1, urate oxidase, EC 1.7.3.3, 3-aci-nitropropanoate oxidase, sulfite oxidase, EC 1.8.3.1, methanethiol oxidase, EC 1.8.3.4, prenylcysteine oxidase, EC 1.8.3.5, L-ascorbate oxidase, EC 1.10.3.3, 3-hydroxyanthranilate oxidase, EC 1.10.3.5, rifamycin-B oxidase, EC 1.10.3.6, superoxide dismutase, EC 1.15.1.1, reticuline oxidase, EC 1.21.3.3, lactate oxidase, L-EC 1.1.3.15, D-amino acid oxidase, EC 1.4.3.3, (S)-6-hydroxynicotine oxidase, EC 1.5.3.5, (R)-6-hydroxynicotine oxidase, EC 1.5.3.6, alcohol oxidase, EC 1.1.3.13, pyruvate oxidase, EC 1.2.3.3, glucose oxidase, EC 1.1.3.4), L-glutamate oxidase, EC 1.4.3.11, acyl coenzyme A oxidase, EC 1.3.3.6, choline Oxidase, EC 1.1.3.17, glutathione sulfhydryl oxidase, EC 1.8.3.3, glycerolphosphate oxidase, EC 1.1.3.21, sarcosine oxidase, EC 1.5.3.1, xanthine oxidase, EC 1.1.3.22, oxalate oxidase, EC 1.2.3.4, co-factor(s)=Mn$^{2+}$; cholesterol oxidase, EC 1.1.3.6, gamma-glutamyl-putrescine oxidase, EC undefined, obtained from *Escherichia coli* K12, capable of oxidizing GABA; GABA oxidase, EC undefined, obtained from: *Penicillium* sp. KAIT-M-117, histamine oxidase (diamine oxidase), EC 1.4.3.22, nucleoside oxidase, EC 1.1.3.39, L-lysine oxidase, EC 1.4.3.14, L-aspartate oxidase, EC 1.4.3.16, glycine oxidase, EC 1.4.3.19, galactose oxidase, EC 1.1.3.9.

In some embodiments, the oxidase enzymes used may be: Lactate oxidase (EC 1.1.3.15), D-amino acid oxidase (EC 1.4.3.3), (S)-6-Hydroxynicotine oxidase (EC 1.5.3.5), (R)-6-Hydroxynicotine oxidase (EC 1.5.3.6), Alcohol oxidase (EC 1.1.3.13), Pyruvate oxidase (EC 1.2.3.3), Glucose oxidase (EC 1.1.3.4), Glutamate oxidase (EC 1.4.3.11), Acyl coenzyme A oxidase (EC 1.3.3.6), Choline oxidase (EC 1.1.3.17), Glutathione Sulfhydryl oxidase (EC 1.8.3.3), Glycerolphosphate oxidase (EC 1.1.3.21), Sarcosine oxidase (EC 1.5.3.1), Xanthine oxidase (EC 1.1.3.22), Oxalate oxidase (EC 1.2.3.4), Cholesterol oxidase (EC 1.1.3.6), Gamma-glutamyl-putrescine oxidase (EC undefined), GABA oxidase (EC undefined), Histamine oxidase (Diamine oxidase, EC 1.4.3.22), Nucleoside oxidase (EC 1.1.3.39), L-Lysine oxidase (EC 1.4.3.14), L-Aspartate oxidase (EC 1.4.3.16), Glycine oxidase (EC 1.4.3.19), and Galactose oxidase (EC 1.1.3.9). GABA is defined as gamma alpha-butyric acid.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A sensor, comprising:
   a masking layer deposited onto a substrate comprising a plurality of electrodes, wherein the masking layer covers the plurality of electrodes;
   an adhesion promoter deposited onto the substrate and onto the masking layer, wherein deposition of the adhesion promoter onto the plurality of electrodes is avoided due to the masking layer;
   a signal transduction enzyme spin coated onto the substrate after the masking layer is removed from the substrate being coated with the adhesion promoter,
      wherein the signal transduction enzyme is configured to detect an active compound capable of generating an electric current, and
      wherein the signal transduction enzyme is configured so that a current measured by the plurality of electrodes settles within about 5% of its stable value within one second; and
   a crosslinker deposited onto the signal transduction enzyme for crosslinking the signal transduction enzyme to produce a cross-linked enzyme film having a thickness of less than one micrometer.

2. The sensor of claim 1, further comprising a solvent with at least one non-reactive component, wherein the signal transduction enzyme is mixed in the solvent prior to the signal transduction enzyme being spin coated onto the substrate.

3. The sensor of claim 2, wherein the at least one non-reactive component comprises a filler, a buffer salt to regulate pH, or both the filler and the buffer salt.

4. The sensor of claim 3, wherein the step of crosslinking the signal transduction enzyme is performed by:
   placing the substrate, coated with the signal transduction enzyme, and the crosslinker in a vacuum chamber; and
   reducing pressure within the vacuum chamber, thereby causing the crosslinker to vaporize and deposit onto the signal transduction enzyme.

5. The sensor of claim 2, wherein the solvent is water.

6. The sensor of claim 5, wherein the signal transduction enzyme is an oxidase enzyme.

7. The sensor of claim 1, wherein the signal transduction enzyme is selected from the group consisting of: malate oxidase, hexose oxidase, aryl-alcohol oxidase, L-gulonolactone oxidase, pyranose oxidase, L-sorbose oxidase, pyridoxine 4-oxidase, (S)-2-hydroxy-acid oxidase, ecdysone oxidase, secondary-alcohol oxidase, 4-hydroxymandelate oxidase, long-chain-alcohol oxidase, thiamine oxidase, hydroxyphytanate oxidase, N-acylhexosamine oxidase, polyvinyl-alcohol oxidase, D-Arabinono-1,4-lactone oxidase, vanillyl-alcohol oxidase, D-mannitol oxidase, alditol oxidase, choline dehydrogenase, gluconate 2-dehydrogenase, glucooligosaccharide oxidase, alcohol dehydrogenase, cellobiose dehydrogenase, aldehyde oxidase, glyoxylate oxidase, indole-3-acetaldehyde oxidase, aryl-aldehyde oxidase, retinal oxidase, abscisic-aldehyde oxidase, aldehyde ferredoxin oxidoreductase, indolepyruvate ferredoxin oxidoreductase, aldehyde dehydrogenase, dihydroorotate oxidase, acyl-CoA oxidase, dihydrouracil oxidase, tetrahydroberberine oxidase, tryptophan alpha, beta-oxidase, L-galactonolactone oxidase, acyl-CoA dehydrogenase, Isoquinoline-1-oxidoreductase, quinaldate 4-oxidoreductase, D-aspartate oxidase, L-amino-acid oxidase, monoamine oxidase, pyridoxal 5'-phosphate synthase, D-glutamate oxidase, ethanolamine oxidase, putrescine oxidase, cyclohexylamine oxidase, protein-lysine 6-oxidase, L-lysine 6-oxidase, primary-amine oxidase, 7-chloro-L-tryptophan oxidase, N-methyl-L-amino-acid oxidase, non-specific polyamine oxidase, N8-acetylspermidine oxidase, N6-methyl-lysine oxidase, polyamine oxidase, N1-acetylpolyamine oxidase, spermine oxidase, pipecolate oxidase, dimethylglycine oxidase, polyamine oxidase, Dihydrobenzophenanthridine oxidase, urate oxidase, 3-aci-nitropropanoate oxidase, sulfite oxidase, methanethiol oxidase, prenylcysteine oxidase, L-ascorbate oxidase, 3-hydroxyanthranilate oxidase, rifamycin-B oxidase, superoxide dismutase, reticuline oxidase, lactate oxidase, D-amino acid oxidase, (S)-6-hydroxynicotine oxidase, (R)-6-hydroxynicotine oxidase, alcohol oxidase, pyruvate oxidase, glucose oxidase, L-glutamate oxidase, acyl coenzyme A oxidase, choline oxidase, glutathione sulfhydryl oxidase, glycerolphosphate oxidase, sarcosine oxidase, xanthine oxidase, oxalate oxidase, cholesterol oxidase, gamma-glutamyl-putrescine oxidase, GABA oxidase, histamine oxidase, nucleoside oxidase, L-lysine oxidase, L-aspartate oxidase, glycine oxidase, and galactose oxidase.

8. The sensor of claim 1, wherein the signal transduction enzyme is selected from the group consisting of: Lactate oxidase, D-amino acid oxidase, (S)-6-Hydroxynicotine oxidase, (R)-6-Hydroxynicotine oxidase, Alcohol oxidase, Pyruvate oxidase, Glucose oxidase, Glutamate oxidase, Acyl coenzyme A oxidase, Choline oxidase, Glutathione Sulfhydryl oxidase, Glycerolphosphate oxidase, Sarcosine oxidase, Xanthine oxidase, Oxalate oxidase, Cholesterol oxidase, Gamma-glutamyl-putrescine oxidase, GABA oxidase, Histamine oxidase, Nucleoside oxidase, L-Lysine oxidase, L-Aspartate oxidase, Glycine oxidase, Urate oxidase, and Galactose oxidase.

9. The sensor of claim 1, wherein the crosslinker is glutaraldehyde.

10. The sensor of claim 1, wherein the adhesion promoter is an inorganic-organic amine coupler.

11. The sensor of claim 1, wherein the substrate comprises silicon.

12. The sensor of claim 1, where the adhesion promoter is an aminosilane.

13. The sensor of claim 1, where the adhesion promoter is 3-aminopropyltriethoxysilane (APTES) or 3-aminopropyltrimethoxysilane (APTMS).

14. The sensor of claim 1, wherein the plurality of electrodes comprises a working electrode, a reference electrode and a counter electrode.

* * * * *